United States Patent
Wagh

(10) Patent No.: US 7,553,480 B2
(45) Date of Patent: Jun. 30, 2009

(54) TOPICAL PERSONAL CARE COMPOSITIONS AND METHODS OF USE

(75) Inventor: Asher Wagh, Brooklyn, NY (US)

(73) Assignee: Pure USA, LLC, East Brunswick, NJ (US)

( * ) Notice: Subject to any disclaimer, the term of this patent is extended or adjusted under 35 U.S.C. 154(b) by 937 days.

(21) Appl. No.: 11/054,883

(22) Filed: Feb. 10, 2005

(65) Prior Publication Data

US 2006/0177471 A1    Aug. 10, 2006

(51) Int. Cl.
*A61Q 5/02* (2006.01)
*A61Q 19/10* (2006.01)

(52) U.S. Cl. .............. 424/70.19; 424/70.21; 424/70.31; 424/70.1; 424/47; 424/401

(58) Field of Classification Search ................. None
See application file for complete search history.

(56) References Cited

U.S. PATENT DOCUMENTS

| | | | |
|---|---|---|---|
| 2,438,091 | A | 3/1948 | Lynch et al. |
| 2,528,378 | A | 10/1950 | Mannheimer |
| 2,658,072 | A | 11/1953 | Kosmin |
| 4,185,106 | A | 1/1980 | Dittmar et al. |
| 4,472,421 | A | 9/1984 | Buchel et al. |
| 4,835,148 | A | 5/1989 | Barford et al. |
| 5,665,364 | A | 9/1997 | McAtee et al. |

*Primary Examiner*—Jyothsna A Venkat
(74) *Attorney, Agent, or Firm*—Fox Rothschild LLP; Gerard P. Norton, Esq.

(57) ABSTRACT

Topical personal care compositions comprising an anti-inflammatory agent, an amphoteric surfactant, a bodifier/humectant, and water and methods of use are disclosed.

3 Claims, No Drawings

TOPICAL PERSONAL CARE COMPOSITIONS AND METHODS OF USE

BACKGROUND OF THE INVENTION

Topical personal care compositions containing the anti-inflammatory agent cortisone are well known in the art. Adrenal corticosteroids, and the synthetic analogues thereof, are active pharmaceutical compounds with the known characteristic of preventing the development of, or suppressing existing, localized heat, redness, tenderness and swelling which characterizes any inflammation of skin or mucous membrane, regardless of the causal factor. The unique biochemical, pharmacologic and physiologic properties of corticosteroids make them extremely useful in the topical treatment of inflammatory conditions in subjects.

It is known that anti-inflammatory agents are effective in the treatment of various skin and scalp disorders such as psoriasis, seborrhea, dermatitis, dandruff, and the like. However, these compounds generally have been available in non-rinse vehicles which contain oils or emulsions which give the hair or skin a soiled appearance.

Surfactants may be added to an anti-inflammatory agent containing formulations to improve the appearance of hair and scalp. For example, U.S. Pat. No. 4,835,148, describes a shampoo composition comprising a water insoluble anti-inflammatory agent and an anionic surfactant. U.S. Pat. No. 5,665,364, describes a topical personal care composition comprising both an anionic surfactant and an amphoteric surfactant, and an active ingredient, one of which may be hydrocortisone. While the addition of an anionic surfactant has been shown to decrease the oily appearance of the hair, it is not considered to be a gentle cleanser and can overstrip the hair and dry the scalp. Therefore, there is a need to provide a topical personal care composition that combines an anti-inflammatory agent with an amphoteric surfactant, providing anti-dandruff and scalp treatment in a mild cleansing composition that is gentle on the hair and scalp, resulting in a more cosmetically desirable appearance.

SUMMARY OF THE INVENTION

One or more embodiments of the present invention relate to topical personal care compositions comprising an effective amount of an anti-inflammatory agent, an effective amount of an amphoteric surfactant, an effective amount of a bodifier/humectant, and water.

Certain embodiments of the present invention pertain to providing a gentle cleanser with a decreased likelihood of irritancy, while still allowing for a level of lather production that is acceptable to the consumer. While embodiments of the invention should not be limited by a particular principle, it is believed that these characteristics may be achieved in the current composition through the use of an amphoteric surfactant as the cleansing agent. Certain embodiments of the present invention provide topical personal care compositions which contain a mild cleanser and do not overstrip the hair and/or dry the skin.

Embodiments of the present invention also relate to increasing the diameter of the hair shaft as well as moderating damage to the hair caused by environmental or other factors. This result may be effectuated though the use of a bodifier/humectant that is sorbable onto or into the shafts of the hair and is able to remain with the hair for a reasonable period of time. Additionally, the bodifier/humectant is believed to decrease the friction between individual shafts of hair, thereby decreasing abrasion damage caused by brushing or combing. This embodiment of the present invention provides topical personal care compositions containing a cosmetically effective amount of a bodifier/humectant that can both increase the diameter of the hair shafts and moderate damage to the hair.

DETAILED DESCRIPTION

One or more embodiments of the invention pertain to topical personal care compositions which are applied to hair and/or skin. In one aspect of the invention the topical personal care composition is worked through wet hair, and later rinsed off to provide the consumer with a scalp treatment in a mild cleansing composition that is gentle on the hair and scalp. In some aspects of the present invention the topical personal care compositions are selected from the group consisting essentially of a body wash, cream, lotion, spray or shampoo.

According to one embodiment of the invention, the topical personal care composition comprises about 0.1% to about 5.0% of an anti-inflammatory agent; about 15.0% to about 55.0% of an amphoteric surfactant; about 0.1% to about 9.0% of bodifier/humectant; and water. In another embodiment of the invention, the anti-inflammatory agent in the above composition includes hydrocortisone. In yet another embodiment of the invention, the amphoteric surfactant in the above composition includes cocamidopropyl hydroxysultaine. In a further embodiment of the invention, the bodifier/humectant includes panthenol, panthenyl ethyl ether, or phytantriol, or mixtures thereof.

In still another embodiment, the anti-inflammatory agent includes hydrocortisone, the amphoteric surfactant includes cocamidopropyl hydroxysultaine, and the bodifier/humectant includes a mixture of panthenol, panthenyl ethyl ether, and phytantriol.

In a further embodiment of the invention, the composition comprises: about 0.1% to about 5.0% hydrocortisone; about 15.0% to about 55.0% cocamidopropyl hydroxysultaine; about 0.1% to about 9.0% panthenol, about 0.1% to about 9.0% panthenyl ethyl ether, and about 0.1% to about 9.0% phytantriol; and about 25.0% to about 70.0% water.

In still another embodiment of the invention, the composition is composed of: about 0.9% to about 1.1% hydrocortisone; about 30% to about 40% cocamidopropyl hydroxysultaine; about 1.0% to about 5.0% panthenol, about 0.5% to about 0.9% panthenyl ethyl ether, and about 0.1% to about 0.5% phytantriol; and about 25.0% to about 70.0% water.

Another aspect of the invention concerns a method of shampooing hair wherein an effective amount of an anti-inflammatory agent is deposited on the scalp comprising the steps of: (a) applying an effective amount of the topical personal care composition to hair that has been wetted; (b) working said composition through said hair; and (c) rinsing said composition from said hair.

According to one or more embodiments of this method aspect, the compositions comprise at least about 0.1% to about 5.0% of an anti-inflammatory agent. Preferably the amount is from about 0.5% to about 2.5%, more preferably from about 0.9% to about 1.1%.

Any type of known anti-inflammatory agent may be useful in compositions of the present invention. A preferred category of anti-inflammatory agents is the adrenal corticosteroids. Most preferred is hydrocortisone, a known anti-inflammatory agent which exists and is commercially available.

One component of the present compositions is an amphoteric surfactant, which is for the delivery of conditioning agents to the hair and skin. A preferred amphoteric surfactant is cocamidopropyl hydroxysultaine. Amphoterics (also known as surface-active agents) possess both a positive and a negative electrical charge and are capable of reacting as either an acid or an alkali, depending upon the rest of the formula. They are promoted to cosmetic manufacturers (and thus indirectly to consumers) as being milder and more desirable than the anionic surfactants.

According to one or more embodiments of this method aspect, the compositions comprise at least about 15.0% to about 55.0% of an amphoteric surfactant. Preferably the amount is from about 30.0% to about 40.0%.

Further examples of amphoteric surfactants which can be used in the compositions of embodiments of the present invention are those broadly described as derivatives of aliphatic secondary and tertiary amines in which the aliphatic radical can be straight chain or branched and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecyl-aminopropionate, sodium 3-dodecylaminopropane sulfonate, N-alkyltaurines such as the one prepared by reacting dodecylamine with sodium isothionate according to the teaching of U.S. Pat. No. 2,658,072, N-higher alkyl aspartic acid esters such as those produced according to the teaching of U.S. Pat. No. 2,438,091, and the products sold under the trade name "Miranol" and described in U.S. Pat. No. 2,528,378.

Certain embodiments of the invention incorporate a bodifier/humectant that increases the diameter of the hair shafts and moderates the damage that environmental or other factors may have caused to hair or skin. The bodifier remains with the hair and skin for a reasonable length of time to minimize future damage. One preferred bodifier is comprised of panthenol, panthenyl ethyl ether, phytantriol, or mixtures thereof, and will comprise an effective amount of a bodifier/humectant, generally about 0.1% to about 9.0% by weight of the composition. The bodifier/humectant according to certain embodiments of the present invention is also effective in moisturizing the skin.

According to one or more embodiments of this method aspect, the compositions comprise at least about 0.1% to about 9.0% of a bodifier/humectant. Preferably the amount is from about 0.1% to about 5.0%.

Water is also an ingredient in the compositions according to embodiments of the present invention. According to one or more embodiments, the compositions contain from about 25.0% to about 70.0% water, preferably from about 34.0% to about 62.0%

Additional components of compositions may include, but are not limited to: preservatives, such as sodium benzoate, methylchloroisothiazolinone, and methylisothiazolinone; anti-fungal agents, such as methylparaben and propylparaben; PEG-6000 distearate; lauramide DEA and linoleamide DEA; glycol stearate; and fragrance.

In one or more embodiments of the invention, anti-dandruff agents are also present in the shampoo compositions. Included among such agents are coal tar, sulfur, selenium sulfide, 1-hydroxy pyridones such as those described in U.S. Pat. No. 4,185,106, and azole antimycotics disclosed in British Pat. No. 1,502,144, both of which patents are incorporated herein by reference in their entirety. When present, this additional anti-dandruff agent comprises from about 0.1% to about 7.0% of the composition, preferably from about 0.2% to about 2.0%.

The topical personal care compositions according to certain embodiments of the present invention may also comprise a suspending agent. The suspending agent useful can be one of several agents, such as for example, ethylene glycol esters of fatty acids containing from about 16 to about 22 carbon atoms, preferably from about 16 to about 18 carbon atoms.

In embodiments that utilize ethylene glycol esters, which may include diesters wherein the esters are a mixture of palmitate and stearate. The amount of stearate should be in the range of about 5.0% to about 20.0% or in the range of about 95.0% to about 80.0% with palmitate accounting for the remainder. The amount of stearate is preferably from about 5.1% to about 10.5%. The distearates found to be useful in certain embodiments of the compositions of the present invention range from about 5.0% to about 10.0%.

According to certain embodiments, alkanol amides of fatty acids containing from about 16 to about 22 carbon atoms, preferably from about 16 to about 18 carbon atoms may be useful. Preferred alkanol amides are stearic monoethanolamide stearic diethanolamide, stearic monoisopropanolamide and stearic monoethanolamide stearate. Another useful group of suspending agents are alkyl dimethylamine oxides, wherein the alkyl group contains from about 16 to about 22 carbon atoms such as stearyldimethyl amine oxide.

Mixtures of the above suspending agents may also be used. Compositions according to certain embodiments of the invention comprise from about 2.0% to about 11.0% of the suspending agent, preferably from about 5.0% to about 7.0%.

The topical personal care compositions according to one ore more embodiments of the present invention can contain a variety of other nonessential optional components suitable for rendering such compositions more acceptable. Such conventional optional ingredients are well known to those skilled in the art, e.g., preservatives such as benzyl alcohol, methyl paraben, propyl paraben, methylisothiazolinone and imidazolidinyl urea; thickeners and viscosity modifiers such as amine oxides, block polymers of ethylene oxide and propylene oxide such as Pluronic F88 offered by BASF Wyandotte, fatty alcohols such as cetearyl alcohol, sodium chloride, ammonium chloride, sodium sulfate, polyvinyl alcohol, propylene glycol and ethyl alcohol; hydrotopes such as xylene sulfonate, amine sulfonate, and polyethylene glycol; pH adjusting agents such as citric acid, succinic acid, phosphoric acid, sodium hydroxide, sodium carbonate, etc.; perfumes; dyes; quaternary ammonium compounds such as Polyquaternium 41; and, sequestering agents such as disodium ethylenediamine tetraacetate. Such agents generally are used individually at a level of from about 0.01% to about 10.0%, preferably from about 0.01% to about 5.0% by weight of the composition.

In certain preferred embodiments, the compositions are free of clays and polymeric thickeners. The term "free" as used herein refers to less than about 20 ppm.

The following Examples further describe and demonstrate the preferred embodiments within the scope of the present invention. The Examples are given solely for the purpose of illustration and are not to be construed as limitations of the present invention as many variations thereof are possible without departing from its spirit and scope.

EXAMPLES

Example I

The following composition is representative of the present invention.

| Component | Weight % |
| --- | --- |
| Hydrocortisone | 1.0% |
| Panthenol | 1.0-5% |
| Phytantriol | 0.1-0.5% |
| Panthenyl Ethyl Ether | 0.5-0.9% |
| Cocamidopropyl Hydroxysultaine | 30.0%-40.0% |
| Water | qs |

Example II

The following composition is also representative of the present invention and is prepared as follows:

| Component | Weight % |
| --- | --- |
| 1. Hydrocortisone | 1.0% |
| 2. Water | QS |
| 3. Cocamidopropyl Hydroxysultaine | 30.0%-40.0% |
| 4. PEG-6000 Distearate | 5.0%-10.0% |
| 5. Panthenol | 1.0%-5.0% |
| 6. Lauramide DEA | 1.0%-5.0% |
| 7. Panthenyl Ethyl Ether | 0.5%-0.9% |
| 8. Lauramide DEA (and) Linoleamide DEA | 0.5%-0.9% |
| 9. Glycol Stearate | 0.1%-0.5% |
| 10. Fragrance | 0.1%-0.5% |
| 11. Phytantriol | 0.1%-0.5% |
| 12. Methylparaben | 0.1%-0.3% |
| 13. Propylparaben | 0.1%-0.3% |
| 14. Sodium Benzoate | 0.1%-0.3% |
| 15. Methylchloroisothiazolinone | <0.1% |
| 16. Methylisothiazolinone | <0.1% |

The composition of Example II is prepared according to the following procedure:

In step 1 of this method of manufacture water is heated to 75° C. and panthenol, lauramide DEA, panthenyl ethyl ether, phytantriol, and methylchloroisothiazolinone are added. The reaction components of step 1 are mixed and the temperature is maintained at 75° C.

In step 2 of the method of manufacture according to this embodiment of the invention, components cocamidopropyl hydroxysultaine, PEG-6000 distearate, glycol stearate, methylparaben, and propylparaben are mixed and heated to 75° C. until the components are dissolved. The resultant reaction mixture of step 2 is then added to the final mixture of step 1. The composition is continually mixed while cooling to 40° C.

In step 3 of the method of manufacture according to this embodiment of the invention, hydrocortisone and water are premixed and added to the resultant composition of step 2.

In step 4 of the method of manufacture according to this embodiment of the invention, components water and sodium benzoate are premixed and added to the resultant composition of step 3.

In step 5 of the method of manufacture according to this embodiment of the invention, lauramide DEA (and) linoleamide DEA, and fragrance are added to the resultant composition of step 4.

What is claimed is:

1. A topical personal care composition consisting of
    1. Hydrocortisone 1.0%
    2. Water QS
    3. Cocoamidopropyl Hydroxysultaine 30.0%-40.0%
    4. PEG-6000 Distearate 5.0%-10.0%
    5. Panthenol 1.0%-5.0%
    6. Lauramide DEA 1.0%-5.0%
    7. Panthenyl Ethyl Ether 0.5%-0.9%
    8. Lauramide DEA (and) Linoleamide DEA 0.5%-0.9%
    9. Glycol Stearate 0.1%-0.5%
    10. Fragrance 0.1%-0.5%
    11. Phytantriol 0.1%-0.5%
    12. Methylparaben 0.1%-0.3%
    13. Propylparaben 0.1%-0.3%
    14. Sodium Benzoate 0.1%-0.3%
    15. Methylchloroisothiazolinone <0.1%
    16. Methylisothiazolinone <0.1%.

2. The topical personal care; composition according to claim 1, wherein the topical personal care composition is in a product selected from the group consisting of a shampoo, body wash, cream, spray or lotion.

3. A method of shampooing hair wherein an effective amount of an anti-inflammatory agent is deposited on the scalp comprising the steps of:
    (a) applying the topical personal care composition according to claim 1 to hair that has been wetted;
    (b) working said topical personal care composition through said hair; and
    (c) rinsing said topical personal care composition from said hair.

* * * * *